United States Patent
Chong

(10) Patent No.: US 10,426,337 B2
(45) Date of Patent: Oct. 1, 2019

(54) FLOW IMAGING IN AN OPTICAL COHERENCE TOMOGRAPHY (OCT) SYSTEM

(71) Applicant: SANTEC CORPORATION, Komaki, Aichi (JP)

(72) Inventor: Changho Chong, Los Altos, CA (US)

(73) Assignee: SANTEC CORPORATION, Komaki (JP)

( * ) Notice: Subject to any disclaimer, the term of this patent is extended or adjusted under 35 U.S.C. 154(b) by 37 days.

(21) Appl. No.: 15/611,515

(22) Filed: Jun. 1, 2017

(65) Prior Publication Data
US 2018/0344149 A1    Dec. 6, 2018

(51) Int. Cl.
*A61B 3/14* (2006.01)
*A61B 3/10* (2006.01)
*A61B 3/12* (2006.01)
*A61B 3/00* (2006.01)

(52) U.S. Cl.
CPC ............ *A61B 3/102* (2013.01); *A61B 3/0025* (2013.01); *A61B 3/1233* (2013.01)

(58) Field of Classification Search
CPC ........... A61B 5/0066; A61B 5/05; A61B 8/13; A61B 5/0073; A61B 2576/00; A61B 5/0035; A61B 5/1455; A61B 5/026; A61B 5/0261; A61B 5/0275; A61B 5/0515; A61B 5/6852; A61B 5/725; A61B 8/06; A61B 8/488
USPC ........ 351/221, 222, 243–246, 200, 205, 206
See application file for complete search history.

(56) References Cited

U.S. PATENT DOCUMENTS

| | | |
|---|---|---|
| 4,466,699 A | 8/1984 | Droessler et al. |
| 5,022,745 A | 6/1991 | Zayhowski et al. |
| 5,319,668 A | 6/1994 | Luecke |
| 5,372,135 A | 12/1994 | Mendelson et al. |
| 5,430,574 A | 7/1995 | Tehrani |
| 5,537,162 A | 7/1996 | Hellmuth et al. |
| 5,561,523 A | 10/1996 | Blomberg et al. |
| 5,982,963 A | 11/1999 | Feng et al. |

(Continued)

FOREIGN PATENT DOCUMENTS

| | | |
|---|---|---|
| DE | 10 2011 114 797 A1 | 4/2013 |
| JP | 2006-202543 A | 8/2006 |

(Continued)

OTHER PUBLICATIONS

Changho Chong, et al. "Large Coherence Length Swept Source for Axial Length Measurement of the Eye." Applied Optics 48:10 (2009): D145-150.

(Continued)

*Primary Examiner* — Brandi N Thomas
(74) *Attorney, Agent, or Firm* — Foley & Lardner LLP

(57) ABSTRACT

A method for imaging includes scanning a B scan of a sample N times at a first slice of a sample. N is greater than or equal to 2. The B scan includes a plurality of A scans. A pixel of the first slice has an M number of A scans within the pixel. Each of the A scans have a spectrum range less than a full spectrum range of the light source. A number of pixels per B scan is an approximate B scan length divided by a lateral resolution size of the pixel. The method further includes determine a flow image of the sample using an optical coherence tomography (OCT) signal reflected back from the sample.

20 Claims, 7 Drawing Sheets

(56) References Cited

U.S. PATENT DOCUMENTS

| | | | |
|---|---|---|---|
| 6,070,093 | A | 5/2000 | Oosta et al. |
| 6,111,645 | A | 8/2000 | Tearney et al. |
| 6,134,003 | A | 10/2000 | Tearney et al. |
| 6,160,826 | A | 12/2000 | Swanson et al. |
| 6,275,718 | B1 | 8/2001 | Lempert |
| 6,282,011 | B1 | 8/2001 | Tearney et al. |
| 6,373,632 | B1 | 4/2002 | Flanders |
| 6,421,164 | B2 | 7/2002 | Tearney et al. |
| 6,485,413 | B1 | 11/2002 | Boppart et al. |
| 6,501,551 | B1 | 12/2002 | Tearney et al. |
| 6,564,087 | B1 | 5/2003 | Pitris et al. |
| 6,725,073 | B1 | 4/2004 | Motamedi et al. |
| 7,099,358 | B1 | 8/2006 | Chong |
| 7,231,243 | B2 | 6/2007 | Tearney et al. |
| 7,323,680 | B2 | 1/2008 | Chong |
| 7,324,214 | B2 | 1/2008 | De Groot et al. |
| 7,352,783 | B2 | 4/2008 | Chong |
| 7,382,809 | B2 | 6/2008 | Chong et al. |
| 7,388,891 | B2 | 6/2008 | Uehara et al. |
| 7,400,410 | B2 | 7/2008 | Baker et al. |
| 7,414,779 | B2 | 8/2008 | Huber et al. |
| 7,428,057 | B2 | 9/2008 | De Lega et al. |
| 7,489,713 | B2 | 2/2009 | Chong et al. |
| 7,701,588 | B2 | 4/2010 | Chong |
| 7,725,169 | B2 | 5/2010 | Boppart et al. |
| 7,835,010 | B2 | 11/2010 | Morosawa et al. |
| 7,865,231 | B2 | 1/2011 | Tearney et al. |
| 7,869,057 | B2 | 1/2011 | De Groot |
| 7,884,945 | B2 | 2/2011 | Srinivasan et al. |
| 7,961,312 | B2 | 6/2011 | Lipson et al. |
| 8,036,727 | B2 | 10/2011 | Schurman et al. |
| 8,115,934 | B2 | 2/2012 | Boppart et al. |
| 8,315,282 | B2 | 11/2012 | Huber et al. |
| 8,405,834 | B2 | 3/2013 | Srinivasan et al. |
| 8,500,279 | B2 | 8/2013 | Everett et al. |
| 8,625,104 | B2 | 1/2014 | Izatt et al. |
| 8,690,328 | B1 | 4/2014 | Chong |
| 8,690,330 | B2 | 4/2014 | Hacker et al. |
| 9,163,930 | B2 | 10/2015 | Buckland et al. |
| 2002/0163948 | A1 | 11/2002 | Yoshida et al. |
| 2005/0171438 | A1 | 8/2005 | Chen et al. |
| 2005/0201432 | A1 | 9/2005 | Uehara et al. |
| 2005/0213103 | A1 | 9/2005 | Everett et al. |
| 2006/0105209 | A1 | 5/2006 | Thyroff et al. |
| 2006/0109872 | A1 | 5/2006 | Sanders |
| 2006/0215713 | A1 | 9/2006 | Flanders et al. |
| 2007/0040033 | A1 | 2/2007 | Rosenberg |
| 2007/0076217 | A1 | 4/2007 | Baker et al. |
| 2007/0081166 | A1 | 4/2007 | Brown et al. |
| 2007/0133647 | A1 | 6/2007 | Daiber |
| 2007/0141418 | A1 | 6/2007 | Ota et al. |
| 2007/0263226 | A1 | 11/2007 | Kurtz et al. |
| 2007/0291277 | A1 | 12/2007 | Everett et al. |
| 2008/0097194 | A1* | 4/2008 | Milner ............ A61B 5/0066 600/425 |
| 2008/0269575 | A1 | 10/2008 | Iddan |
| 2009/0022181 | A1 | 1/2009 | Atkins et al. |
| 2009/0103050 | A1 | 4/2009 | Michaels et al. |
| 2009/0169928 | A1 | 7/2009 | Nishimura et al. |
| 2009/0247853 | A1 | 10/2009 | Debreczeny |
| 2009/0268020 | A1 | 10/2009 | Buckland et al. |
| 2009/0290613 | A1 | 11/2009 | Zheng et al. |
| 2010/0157308 | A1 | 6/2010 | Xie |
| 2010/0246612 | A1 | 9/2010 | Shimizu |
| 2010/0284021 | A1 | 11/2010 | Hacker |
| 2011/0112385 | A1 | 5/2011 | Aalders |
| 2011/0235045 | A1 | 9/2011 | Koerner |
| 2011/0255054 | A1 | 10/2011 | Hacker et al. |
| 2011/0299034 | A1 | 12/2011 | Walsh et al. |
| 2012/0026466 | A1 | 2/2012 | Zhou et al. |
| 2012/0136259 | A1 | 5/2012 | Milner et al. |
| 2012/0188555 | A1 | 7/2012 | Izatt et al. |
| 2014/0051952 | A1 | 2/2014 | Reichgott et al. |
| 2014/0111774 | A1 | 4/2014 | Komine |
| 2014/0228681 | A1 | 8/2014 | Jia et al. |
| 2014/0268163 | A1 | 9/2014 | Milner et al. |
| 2014/0293290 | A1 | 10/2014 | Kulkarni |
| 2014/0336479 | A1 | 11/2014 | Ando |
| 2015/0348287 | A1 | 12/2015 | Yi et al. |
| 2016/0178346 | A1 | 6/2016 | Kulkarni |
| 2017/0090031 | A1 | 3/2017 | Bondy et al. |
| 2018/0128594 | A1 | 5/2018 | Lee et al. |

FOREIGN PATENT DOCUMENTS

| | | |
|---|---|---|
| JP | 2008-188047 | 8/2008 |
| JP | 2010-172538 | 8/2010 |
| JP | 2010-540914 A | 12/2010 |
| WO | WO-2012/075126 A2 | 6/2012 |
| WO | WO-2013/168149 A1 | 11/2013 |
| WO | WO-2015/121756 A2 | 8/2015 |

OTHER PUBLICATIONS

Chowdhury, Md Koushik et al., Challenges & Countermeasures in Optical Noninvasive Blood Glucose Detection, International Journal of Innovative Research in Science, Engineering and Technology vol. 2, Issue 1, Jan. 2013 (6 pages).

Dai et al., "Optical coherence tomography for whole eye segment imaging," Optics Express, vol. 20, No. 6 (2012) pp. 6109-6115.

Dhalla et al., "Simultaneous swept source optical coherence tomography of the anterior segment and retina using coherence revival," Optics Letters, vol. 37 No. 11, Jun. 1, 2012, pp. 1883-1885.

English Translation of the International Search Report and Written Opinion on International Application No. PCT/EP2009/009189, dated Apr. 6, 2010, 12 pages.

F. Lexer et al., "Wavelength-tuning interferometry of intraocular distances," Applied Optics, vol. 36, No. 25, pp. 6548-6553 (Sep. 1, 1997).

Fainman, Y. et al., "Nanophotonics for Information Systems," Information Optics and Photonics (T. Fournel and B. Javidi eds., Springer New York, 2010) pp. 13-37.

International Search Report and Written Opinion dated Aug. 26, 2015 for PCT/US15/32727 (8 pages).

International Search Report and Written Opinion in International Application No. PCT/US2015/19299 dated Nov. 2, 2015 (10 pages).

International Search Report and Written Opinion in PCT/IB2015/000808 dated Oct. 20, 2015 (12 pages).

Jeong et al., "Spectral-domain OCT with dual illumination and interlaced detection for simultaneous anterior segment and retina imaging," Optics Express, vol. 20, Issue 17, pp. 19148-19159 (2012).

Jeong et al., Spectral-domain 1-13 OCT with dual illumination and interlaced detection for simultaneous anterior segment and retina imaging, Optics Express, vol. 20 No. 17, dated Aug. 13, 2012, pp. 19148-19159.

Jia et al., Split-Spectrum Amplitude-Decorrelation Angiography with Optical Coherence Tomography, Optics Express, vol. 20 No. 4, Feb. 9, 2012, pp. 4710-4725.

Lexer et al., "Wavelength-tuning interferometry of intraocular distances", Applied Optics, vol. 36, No. 25, Sep. 1, 1997, pp. 6548-6553.

Mariampillai et al., Speckle Variance Detection of Microvasculature Using Swept-Source Optical Coherence Tomography, Optics Letters, vol. 33 No. 13, Jul. 1, 2008, pp. 1530-1532.

Nankivil et al., ◆FFD01CHandheld, rapidly switchable, anterior/posterior segment swept source optical coherence tomography probe,◆ FFD01D OSA Nov. 1, 2015; vol. 6, No. 11; DOI:10.1364/BOE.6.004516; Biomedical Optics Express 4516-4528.

P. Tayebati et al., "Microelectromechanical tunable filter with stable half symmetric cavity," Electronics Letters, vol. 34, No. 20, pp. 1967-1968 (Oct. 1, 1998).

Sarlet, G. et al., "Wavelength and Mode Stabilization of Widely Tunable SG-DBR and SSG-DBR Lasers," IEEE Photonics Technology Letters, vol. 11, No. 11, Nov. 1999, pp. 1351-1353.

(56) References Cited

OTHER PUBLICATIONS

Segawa, Toru et al., "Semiconductor Double-Ring-Resonator-Coupled Tunable Laser for Wavelength Routing," IEEE Journal of Quantum Electronics, vol. 45, No. 7, Jul. 2009, pp. 892-899.
Sergie Ortiz, et al. "Corneal Topography From Spectral Optical Coherence Tomography (SOCT)." Biomedical Optics Express 2:12, (2011):3232-3247.
U.S. Office Action dated Sep. 12, 2013.
U.S. Office Action on U.S. Appl. No. 14/723,325 dated Nov. 18, 2016.
International Preliminary Report on Patentability in corresponding international application No. PCT/US2015/019299 dated Sep. 22, 2016.
International Preliminary Report on Patentability in corresponding international application No. PCT/US2015/032727 dated Dec. 8, 2016.
International Preliminary Report on Patentability in International appln. No. PCT/IB2015/000808.
International Search Report and Written Opinion in corresponding application No. PCT/US2016/035012 dated Aug. 18, 2016.
U.S. Notice of Allowance on 105093-0102 dated Dec. 6, 2013.
U.S. Notice of Allowance on U.S. Appl. No. 14/601,945 dated Sep. 13, 2016.
U.S. Notice of Allowance on U.S. Appl. No. 14/613,644 dated Nov. 7, 2016.
U.S. Notice of Allowance on U.S. Appl. No. 14/613,644 dated Nov. 18, 2016.
U.S. Notice of Allowance on U.S. Appl. No. 14/641,200 dated Jul. 12, 2016.
U.S. Office Action dated Aug. 19, 2015.
U.S. Office Action on U.S. Appl. No. 14/601,945 dated Mar. 2, 2016.
U.S. Office Action on U.S. Appl. No. 14/613,644 dated Jun. 8, 2016.
U.S. Office Action on U.S. Appl. No. 14/641,200 dated Mar. 14, 2016.
U.S. Office Action on U.S. Appl. No. 14/641,200 dated Dec. 7, 2015.
U.S. Office Action on U.S. Appl. No. 14/723,325 dated Apr. 24, 2017.
U.S. Office Action on U.S. Appl. No. 15/202,925 dated Jul. 27, 2017.
Chopra et al., Topographical Thickness of the Skin in the Human Face, Aesthetic Surgery Journal, vol. 35(8), 2015, pp. 1007-1013.
Final Office Action on U.S. Appl. No. 14/723,325 dated Jul. 26, 2018.
International Preliminary Report on Patentability on International Application No. PCT/US2016/035012 dated Dec. 14, 2017 (11 pages).
Non-Final Office Action on U.S. Appl. No. 15/086,520 dated Aug. 6, 2018.
Non-Final Office Action on U.S. Appl. No. 15/139,579 dated Jul. 17, 2018.
Non-Final Office Action on U.S. Appl. No. 15/648,239 dated Jun. 6, 2018.
Non-Final Rejection Office Action on U.S. Appl. No. 14/723,325 dated Dec. 7, 2017 (11 pages).
Poddar, et al., "Non-Invasive Glucose Monitoring Techniques: A Review and Current Trends," Oct. 2008, pp. 1-47.
U.S. Notice of Allowance on U.S. Appl. No. 15/202,925 dated May 17, 2018.
U.S. Office Action on U.S. Appl. No. 15/630,654 dated Apr. 4, 2018.

* cited by examiner

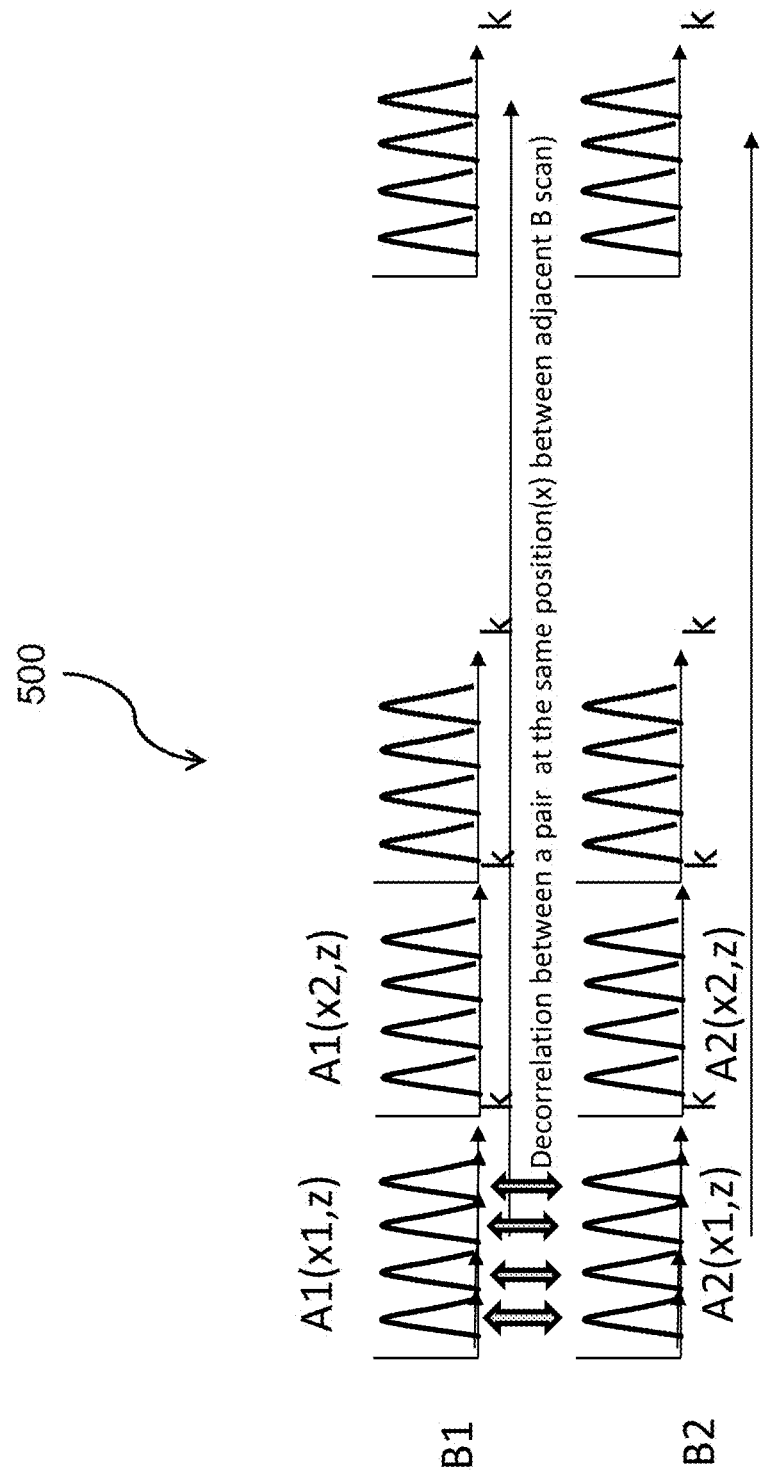

FLOW IMAGING IN AN OPTICAL COHERENCE TOMOGRAPHY (OCT) SYSTEM

BACKGROUND

The following description is provided to assist the understanding of the reader. None of the information provided or references cited is admitted to be prior art.

Optical coherence tomography (OCT) is an imaging technique. OCT imaging techniques are often used in a medical setting. The techniques are capable of producing three dimensional images from within optical scattering samples, such as biological tissue. In other words, light scattered by a sample can be detected in order to form an image of the sample. When imaging a sample, parts of the sample below its surface can be imaged. Examples of biological tissue that may be imaged using OCT include coronary arteries, skin, and an eye. In another example, OCT may be used for art conservation to analyze layers of a painting.

OCT is often accomplished with the use of an interferometer. An interferometer utilizes light that is reflected back from a sample and a reference light. The reference light is generally configured to travel a similar distance as light that is reflected back from the sample. The light from the sample and the reference light can be combined in such a way that gives rise to an interference pattern. That is, the light from the sample and the reference light will either constructively or destructively interfere with each other. The level of interference that occurs indicates the reflectivity of areas of the sample, such that structures within the sample may be identified and imaged.

SUMMARY

In an embodiment, the present technology provides improved flow imaging using an optical coherence tomography (OCT) system. In an illustrative embodiment, the OCT system includes a light source configured to generate a probe beam having an adjustable swept rate and swept range. The OCT system further includes an interferometer and beam scanning optics configured to scan the probe beam onto a sample. The OCT system further includes a detector configured to measure an OCT interference signal returning from the sample. The OCT system further includes a processor configured to generate an OCT image of a flow of the sample. The processor is further configured to scan a B scan of a sample N times at a first slice of the sample. N is greater than or equal to 2. The B scan includes a plurality of A scans. A pixel of the first slice has an M number of A scans within the pixel. Each of the A scans have a spectrum range less than a full spectrum range of the light source. A number of pixels per B scan is an approximate B scan length divided by a lateral resolution size of the pixel. The processor is further configured to determine a flow image of the sample using an optical coherence tomography (OCT) signal reflected back from the sample.

An illustrative method for imaging includes scanning a B scan of a sample N times at a first slice of a sample. N is greater than or equal to 2. The B scan includes a plurality of A scans. A pixel of the first slice has an M number of A scans within the pixel. Each of the A scans have a spectrum range less than a full spectrum range of the light source. A number of pixels per B scan is an approximate B scan length divided by a lateral resolution size of the pixel. The method further includes determine a flow image of the sample using an optical coherence tomography (OCT) signal reflected back from the sample.

An illustrative non-transitory computer readable medium having instructions thereon that, upon execution by a computing device, cause the computing device to perform operations including scanning a B scan of a sample N times at a first slice of a sample. N is greater than or equal to 2. The B scan includes a plurality of A scans. A pixel of the first slice has an M number of A scans within the pixel. Each of the A scans have a spectrum range less than a full spectrum range of the light source. A number of pixels per B scan is an approximate B scan length divided by a lateral resolution size of the pixel. The operations further include determine a flow image of the sample using an optical coherence tomography (OCT) signal reflected back from the sample.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIG. 5 depicts a graph that demonstrates amplitude-decorrelation and speckle variance methods for flow imaging in accordance with an illustrative embodiment.

DETAILED DESCRIPTION

Figure 1:
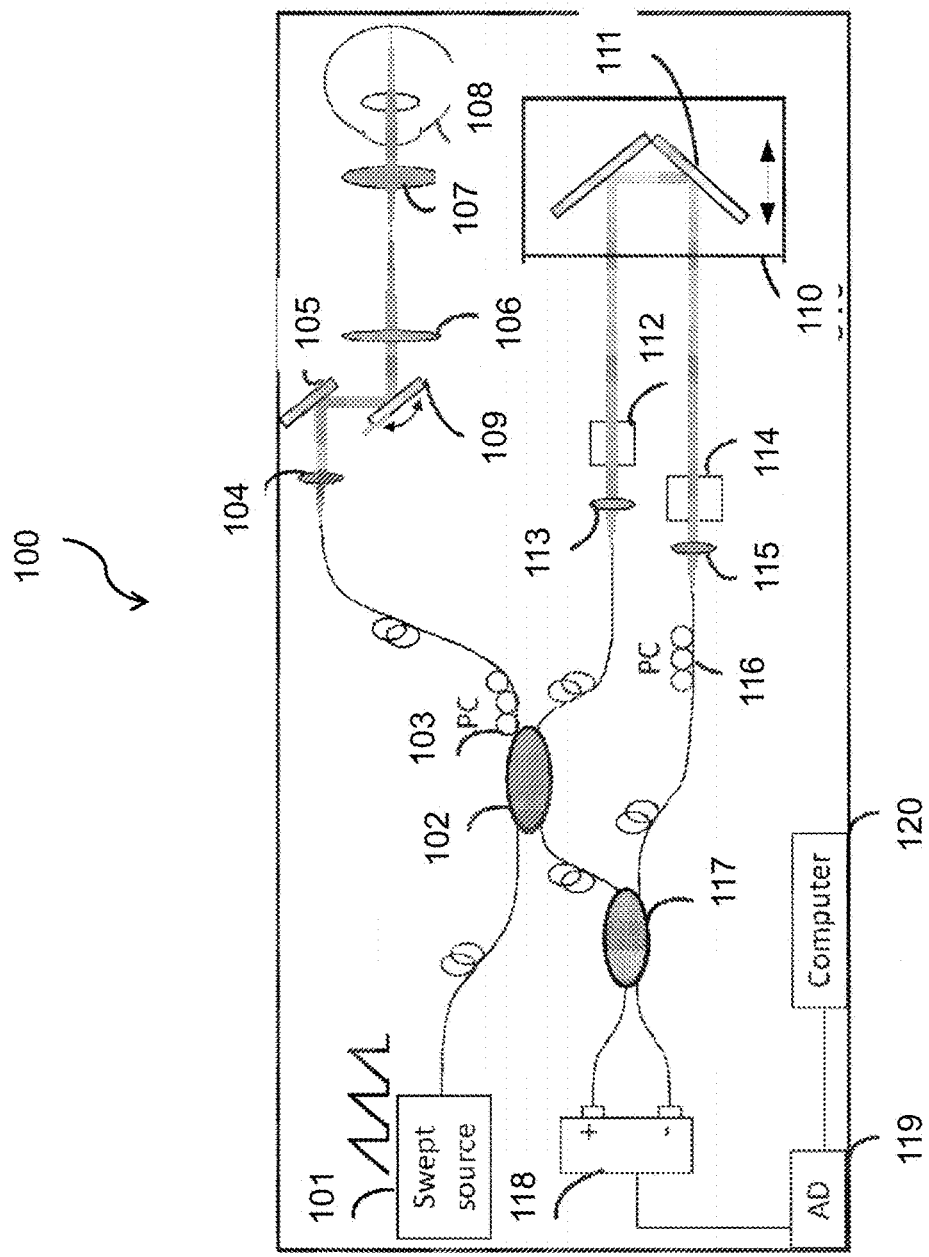
FIG. 1 depicts a representation of an optical coherence tomography (OCT) system in accordance with an illustrative embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Described herein is an improved optical coherence tomography (OCT) system for flow imaging, for example, for imaging of blood flow through vessels in the human eye. In many applications, it is valuable to image structures using OCT systems, such as structures within the human eye (e.g., microcirculation in the human ocular fundus). In addition it can be valuable to image fluid flow using OCT systems, such as through blood vessels in the human eye. In various embodiments, improved systems, methods, and computer readable medium are disclosed herein that offer better resolution and/or faster flow imaging, or vascular network imaging in OCT, in addition to simple structural OCT image based on scattering from a sample.

In an ophthalmic application, for example, such flow imaging, or OCT angiography, may be useful for various diagnostics of macular diseases that can be indicated by the macular vascular (blood vessel) network. There are multiple ways to realize such vascular network imaging in OCT. One method is to use Doppler OCT, which detects a Doppler phase shift in OCT signal reflected back from the sample. However, in order to do this with a swept source OCT, a high level of phase stability of the swept source is important to ensure an accurate measurement of the phase shift of the signal returning from the sample. Without high phase stability, noise and/or other inaccuracies may be introduced into an image.

Another way to perform OCT flow imaging is to use speckle variance detection method or amplitude-decorrelation method. In this approach, phase information is not used, which can simplify a hardware configuration of the OCT system including a swept source. Flow or perfusion of blood is detected by OCT signal intensity differentiation (speckle variance) or by amplitude-decorrelation because there is speckle change in the image over time in the presence of flow. For example, demonstration of a speckle variance detection with a swept source OCT system is described in Mariampillai et al., Speckle Variance Detection of Microvasculature Using Swept-Source Optical Coherence Tomography, Optics Letters, Vol. 33 No. 13, Jul. 1, 2008, which is disclosed herein by reference in its entirety. The basic mode of operation is repeating a beam scan at the same location for several times and calculating the speckle variation (or amplitude-decorrelation) that exists when comparing subsequent images.

The full spectrum decorrelation method described in Mariampillai uses repeated B scans at a same location, which can cause a longer time for signal acquisition. Additionally, detection of flow tends to include bulk-motion noise in an axial direction, which can negatively impact the imaging of transverse blood flow, especially in the case of a retinal blood vessel where the axial resolution of an OCT image is higher than a transverse resolution, which makes it more noise-sensitive to any bulk-motion of the vessel or sample itself.

Another method for flow imaging with an OCT system, called split-spectrum amplitude-decorrelation angiography (SSADA) can also be used. An OCT signal returning from a sample can be split using filters such that the spectrum of a single scan is split into several bands. These bands can be used for multiple variations simultaneously, and can relieve some of the issues described above with respect to Mariampillai. In particular, SSADA does not have to include repeat scans of a sample, thus yielding a shorter scan time and effectively reducing the axial resolution without sacrificing speckle variance information. By reducing the axial resolution through this method, the overall decorrelation signal-to-noise ratio (DSNR) can be improved, yielding better quality flow images. Such a method is described in Jia et al, Split-Spectrum Amplitude-Decorrelation Angiography with Optical Coherence Tomography, Optics Express, Vol. 20 No. 4, Feb. 9, 2012 and U.S. Pat. Pub. No. 2014/0228681, both of which are incorporated herein by reference in their entirety.

U.S. Pat. No. 8,500,279, incorporated herein by reference in its entirety, proposes using two different swept source modes, one for a lower resolution mode for previewing an image area before image acquisition, and a second mode for higher resolution with a full spectrum range of the swept source used for image acquisition.

Disclosed herein are systems, methods, and computer readable medium for improved flow imaging. The OCT systems disclosed herein utilize an agile swept source that can vary a swept source rate and a swept source spectrum range very quickly and flexibly. For example, the OCT system may include a tunable VCSEL that allows such functionality that only changes the drive waveform of the system. Thus, quick switching of the swept source can be accomplished.

Utilizing such a swept source in an OCT system, an illustrative vascular network visualization method changes a swept source rate to be M times faster and the swept range (or spectrum) of each scan to be divided by M so that it actually increases a number of A scans (lines) per B scan by M times. The A scans are combined to form a B scan that corresponds to a slice of a sample. In such a method, the system does not have to filter or band pass the returning signal from the sample, because the returning signal is already broken up into additional scans. In addition, the signals can be more easily combined into a flow image because the scans may all be of the same spectrum range. In addition, similar SSADA data processing methods can be used to assemble the image from the returned scan signals.

Because the swept range may be reduced by factor of 1/M, the axial resolution may be increased by M times, while also increasing A lines/scans by M times. In such an approach, each A scan is repeated in the same way so reshaping does not necessarily have to be performed and the spectrum range used covers the same wavelength range over M times, so the full temporal changes in the speckle variance information is not sacrificed. Accordingly, in various embodiments, spectrum ranges less than a full spectrum of a swept light source can be used advantageously as a signal that is sent to a sample for flow imaging. When that signal is reflected back, it can be processed as disclosed herein to yield a flow image that has better resolution and/or is acquired more quickly than a signal acquired using traditional methods or devices.

FIG. 1 depicts a representation of an optical coherence tomography (OCT) system 100 in accordance with an illustrative embodiment. The OCT system 100 shows just one example of a system that may be used along with the methods and computer readable medium disclosed herein. Other configurations and systems are possible and contemplated. Systems used in various embodiments may have some or additional components than the OCT system 100 of FIG. 1.

A high-speed swept-source OCT system 100 comprises a tunable laser 101. The tunable laser 101 may have, for example, a wavelength of 1050 nm with 100 nm tuning range, a tuning cycle with a repetition rate of up to 400 kHz and a duty cycle of 50%. Other configurations of an OCT system may also be used in various embodiments. Light from the swept source 101, or a probe beam, is coupled into a two by two fiber coupler 102 through single mode optical fiber. As disclosed herein, the swept source generates a signal or probe beam that has an adjustable swept rate and swept range. The OCT system 100 also includes an interferometer and beam scanning optics configured to scan the probe beam onto a sample. Accordingly, one portion of the light proceeds to the sample arm (i.e., the patient interface), and the other portion of the light can proceed to the reference arm.

In the sample arm, a sample arm polarization control unit 103 can be used to adjust light polarization state. The exit light from the fiber coupler 102 is coupled with a retinal scanner whereby the light is collimated by sample arm collimating lens 104 and reflected by mirror 105 and two dimensional galvo scanner 109 (e.g., an XY galvonanometer scanner). Two lenses, first lens 106 (e.g., an objective lens) and second lens 107 (e.g., an ocular lens), relay probe beam reflected by galvo scanner 109 into a human eye 108, although other body parts or things may be scanned also. For example, a focused spot diameter of 18 μm (full-width-half-maximum amplitude profile) can be calculated on the retinal plane based on an eye model. The average light power (i.e., output power of the laser) onto human eye can be 1.9 mW, which is consistent with safe ocular exposure limit set by the American National Standard Institute (ANSI).

The reference arm can comprise a first reference arm collimating lens 113, a water cell 112, a retro-reflector 111, a glass plate 114 and a second reference arm collimating lens 115. The glass plate 114 can be used to balance the dispersion between the OCT sample arm and reference arm. Water cell 112 compensates the influence of dispersion in the human eye 108. The retro-reflector 111 is mounted on a translation stage 110 that can be moved to adjust the path length in the reference arm.

Light from sample and reference arm interfere at beam splitter 117. A reference arm polarization control unit 116 is used to adjust the beam polarization state in the reference arm to maximum interference signal. The optical interference signal from beam splitter 117 is detected by a balanced detector 118, sampled by an analog digital conversion unit 119 and transferred into computer 120 for processing. For example, computer 120 can be used for storing instruction for and implementing the methods described herein. The computer 120 include a processor configured to carry out various processing functions, such as those described herein to generate a flow image. The processor can carry out processing functions according to instructions stored on a memory of the computer 120 or otherwise connected to the computer 120. The memory may be non-transitory computer readable medium having instructions thereon that, upon execution by a computing device or processor, cause the computing device or processor to perform operations. Such operations may include the various processing and/or methods disclosed herein. The memory and instructions thereon may also be executed by a processor to control other aspects of the OCT system 100, such as the swept source. As disclosed herein, the swept source can be switched to perform different imaging modes, resolutions, and/or scan times. Accordingly, the processor and computer 120 may control the various aspects of the OCT system 100 to affect such modes and methods.

Figure 2:
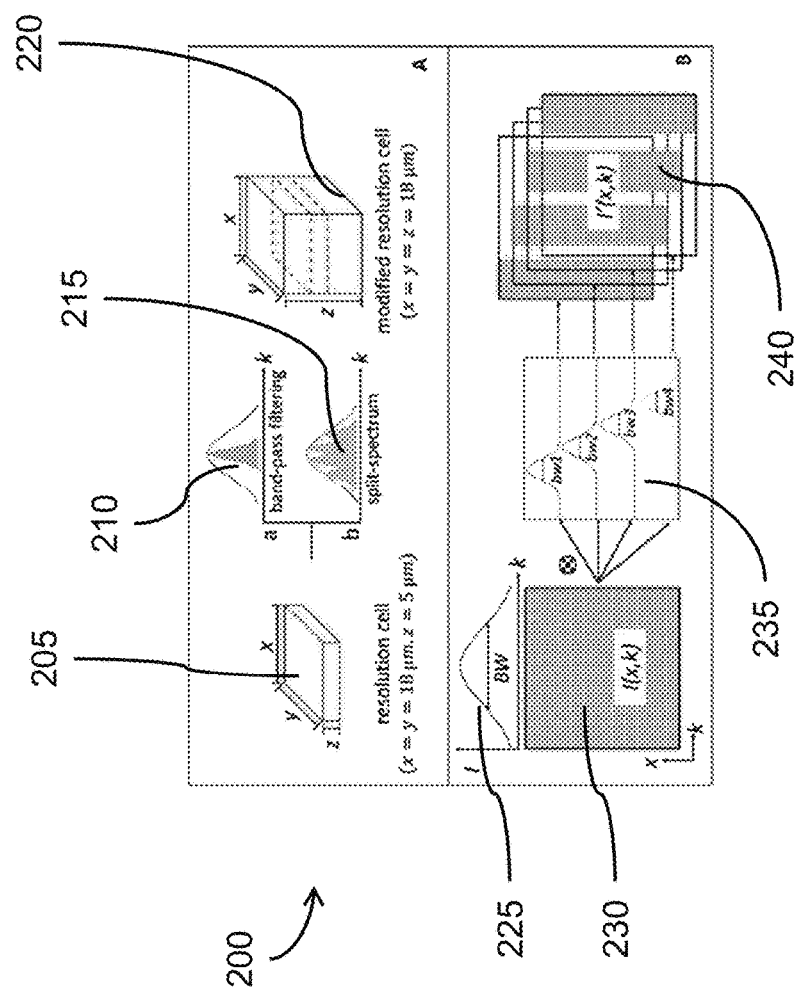
FIG. 2 depicts a representation that demonstrates split-spectrum amplitude-decorrelation angiography (SSADA) in an OCT system.

FIG. 2 depicts a representation that demonstrates split-spectrum amplitude-decorrelation angiography (SSADA) in an OCT system. FIG. 2 shows SSADA that may be achieved using the swept source OCT system 100 of FIG. 1. As merely an example to explain A and B scans, the swept-source OCT system can be operated at 100-kHz axial scan repetition rate. In a fast transverse scan (X) direction, a B scan can include of 200 A scans over 3 mm. In a slow transverse scan (Y) direction, there can be 200 discrete sampling planes over 3 mm. Multiple (N greater than 1) consecutive B scans can then be acquired at each Y position. This is referred to as the M-B-scan mode because it allows detection of motion between consecutive B-scans at the same position. Thus, it may take 3.2 sec to obtain a 3D volumetric data cube comprised of 1600 B-scans and 32,000 A-scans. Finally, the 200 calculated B-scan frames can be combined to form 3D blood perfusion images of posterior part of the human eye. As will be disclosed herein, the methods and systems described below can be used to modify such an approach to increase the resolution of a flow image and/or speed up the time it takes to acquire scans for a flow image. As discussed herein, the flow image from such information may be determined in various ways, such as speckle variance detection, amplitude-decorrelation, or averaging speckle variance or amplitude-decorrelation across multiple scans.

FIG. 2 shows two techniques (band-pass filtering 210 and split-spectrum 215) to create an isotropic resolution cell 220. Each pixel in a B scan OCT image is formed from back-scattered signals of a 3D volume in space, where a pixel is sometimes referred to as a resolution cell (e.g., imaging resolution cell 205 in FIG. 2). The statistical changes in the envelope intensity are related to the motion of scatterers through the OCT resolution cell. For a swept-source OCT setup, an axial (Z direction) resolution, determined by the source central wavelength and its spectral bandwidth, is much higher than the lateral resolution determined by the laser beam profile in both X and Y directions. For example, in swept source OCT systems, using the full-width-half-maximum (FWHM) amplitude profile definition, the axial resolution (~5 μm) is four times higher than the lateral resolution (~18 μm) if both are defined as full-width-half-maximum amplitude profiles (e.g., imaging resolution cell 205 depicts x=y=4z). This anisotropic resolution cell, with higher axial than transverse resolution, will result in higher decorrelation sensitivity for axial motion. In the fundus, ocular pulsation related to heart beat, driven by the retrobulbar orbital tissue, mainly occurs along the axial direction. The anisotropic resolution cell of retinal OCT imaging is very sensitive to this axial motion noise. On the other hand, retinal and choroidal blood flow vectors are primarily transverse to the OCT beam, along the wider (less sensitive) dimensions of the OCT resolution cell. Therefore, to improve the signal-to-noise ratio (SNR) of flow detection, it is desirable to lower the axial resolution and dampen the axial decorrelation sensitivity. This reduces the axial motion noise without sacrificing the transverse flow signal.

One way to achieve this resolution modification is band-pass filtering of the spectral interferogram (e.g., band-pass filtering 210). However, this sacrifices speckle information in the spectral interferogram and decreases the flow signal. Another way to decrease axial resolution that does not lose as much speckle information is to split the spectrum into different frequency bands (e.g., split-spectrum 215) and calculate decorrelation in each band separately. The decorrelation (flow) images from the multiple spectral bands can then be averaged together to make full use of the speckle information in the entire OCT spectrum. The lower half of FIG. 2 shows this process in more detail. Intensity information 230 received from a signal that has reflected from a sample and represents a full bandwidth 225 of a swept source is split into different frequency bands 235. The different frequency bands 235 can be processed to yield different decorrelation images between each B scan, which can be averaged to increase decorrelation signal-to-noise (SNR) ratio of the lateral (x) and axial (z) directions. Accordingly, the split spectrum can yield improved imaging without increasing scan time. However, such methods can introduce errors due to difficulties in reshaping the bands back together to form a flow image, especially considering a non-uniform full spectrum of the swept source used for A scans. The influence of different absorption spectrums in between split bands can also give additional noise contribution to an image.

Figure 3:
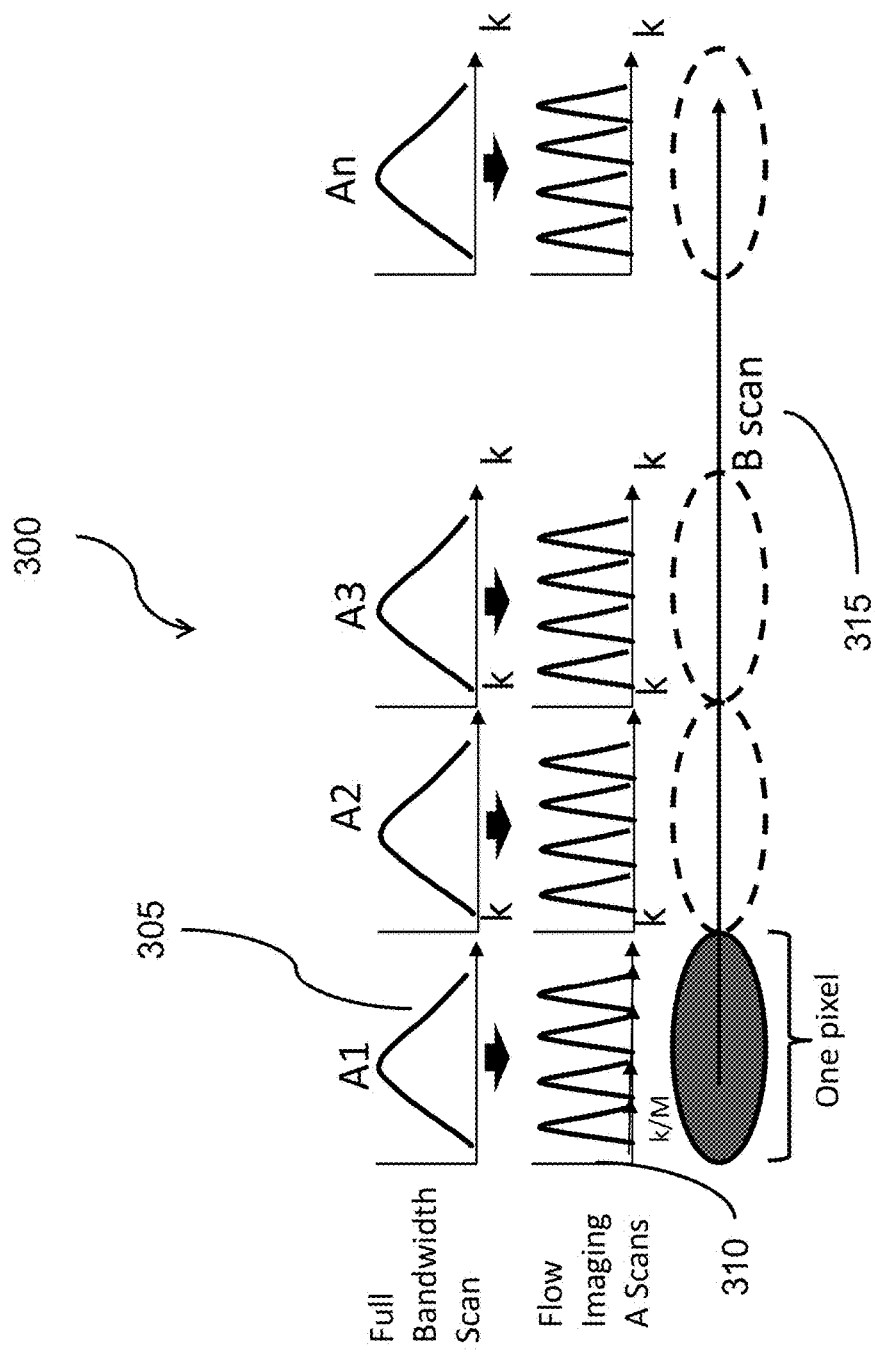
FIG. 3 depicts a graph that demonstrates flow imaging in accordance with an illustrative embodiment.

FIG. 3 depicts a graph 300 that demonstrates flow imaging in accordance with an illustrative embodiment. Instead of splitting the spectrum into different bands after sending and receiving a full spectrum signal that has reflected from a sample, the method disclosed herein shows sending multiple A scans 310 instead of one single A scan that covers a full-spectrum bandwidth of a swept source. These multiple A scans can be sent a higher rate or frequency than the full bandwidth scan so that the additional scans do not take longer. For example, in FIG. 2 above, the scans or probe beams were sent at 100 kHz and had a wavelength of 100 nm. In the method shown in FIG. 3, the A scans 310 may have a frequency of 400 kHZ and a wavelength of 25 nm. In this way, the four A scans 310 shown in FIG. 3 take just as long as a full bandwidth scan of the example in FIG. 2. The four A scans 310, in this example, correspond to a pixel, and a series of the A scans 310 make up a B scan 315. Accordingly, each A scan uses less than the full spectrum of the swept source of an OCT system. Additionally, each of the A scans may have the same bandwidth, reducing reshaping errors when the flow image is formed. The methods disclosed here also provide for simpler signal processing. For example, the multiple band pass filters utilized to accomplish the results of FIG. 2 may not be present or utilized when practicing the method of FIG. 3. This method of increasing a number M of the A scans 310 occurs through fast switching of the swept source. In an alternative embodiment, the system may vary the spectrum range for each or some of the A scans.

Also shown is a full bandwidth scan 305, similar to the one described above with respect to the split spectrum method of FIG. 2. As can be seen, there are four A scans 130 for every one of the full bandwidth scans 305. In this way, the system can scan just as much and collect just as much reflection information from a sample, but reduce some of the errors and difficulties in piecing that data together into a flow image. Flow images can therefore be improved by splitting the A scan into multiple scans before it is sent to the sample.

In this embodiment, the B scan 315 is shown scanning a sample N times at a first slice of the sample. More than one B scan can be performed, such that N is greater than or equal to 2, but only one B scan 315 is actually shown in FIG. 3. For example, B scans adjacent to the slice of the sample may be performed. In addition, more B scans at the location of the first slice may also be performed in some embodiments. The B scan includes a plurality of A scans 310. A pixel of the first slice has an M number of A scans within the pixel. In FIG. 3, M=4, and the spectrum range of each of the A scans is approximately 1/M of the full spectrum of the light source. M may be any non-zero positive integer. For the method of FIG. 3, M is 2 or more. However, M may also be 1, as described below in the embodiment shown in FIG. 4. In this embodiment, though, the A scans still have a spectrum range less than the full spectrum of the swept light source of the OCT system. Each, e.g. B scan 315, has a number of pixels that equals an approximate B scan length divided by a lateral resolution size of the pixel (or resolution cell). Although the signal sent to the sample in the method of FIG. 3 is different to the signals of FIG. 2, the signals of FIG. 3 can still yield a resolution cell with similar dimensions and resolution to the resolution cell 220 of FIG. 3. Once the system has received the OCT signal reflected back from the sample, the system can determine a flow image of the sample.

This determination of the flow image may be done in a number of ways as disclosed herein. For example, the system can determine the flow image by performing speckle variance detection or amplitude-decorrelation of the OCT signal between corresponding A scans of the same spectrum range within a pixel. The system can also determine the flow image by performing speckle variance detection or amplitude-decorrelation of the OCT signal of the M number of A scans. In some embodiments, the system can determine the flow image by performing speckle variance detection or amplitude-decorrelation of the OCT signal between the consecutive N B scans at the pixel. In yet another example, the system may determine the flow image by averaging speckle variance detection or amplitude-decorrelation of the OCT signal over the M A scans of the pixel and/or over consecutive N B scans at the pixel.

Figure 4:
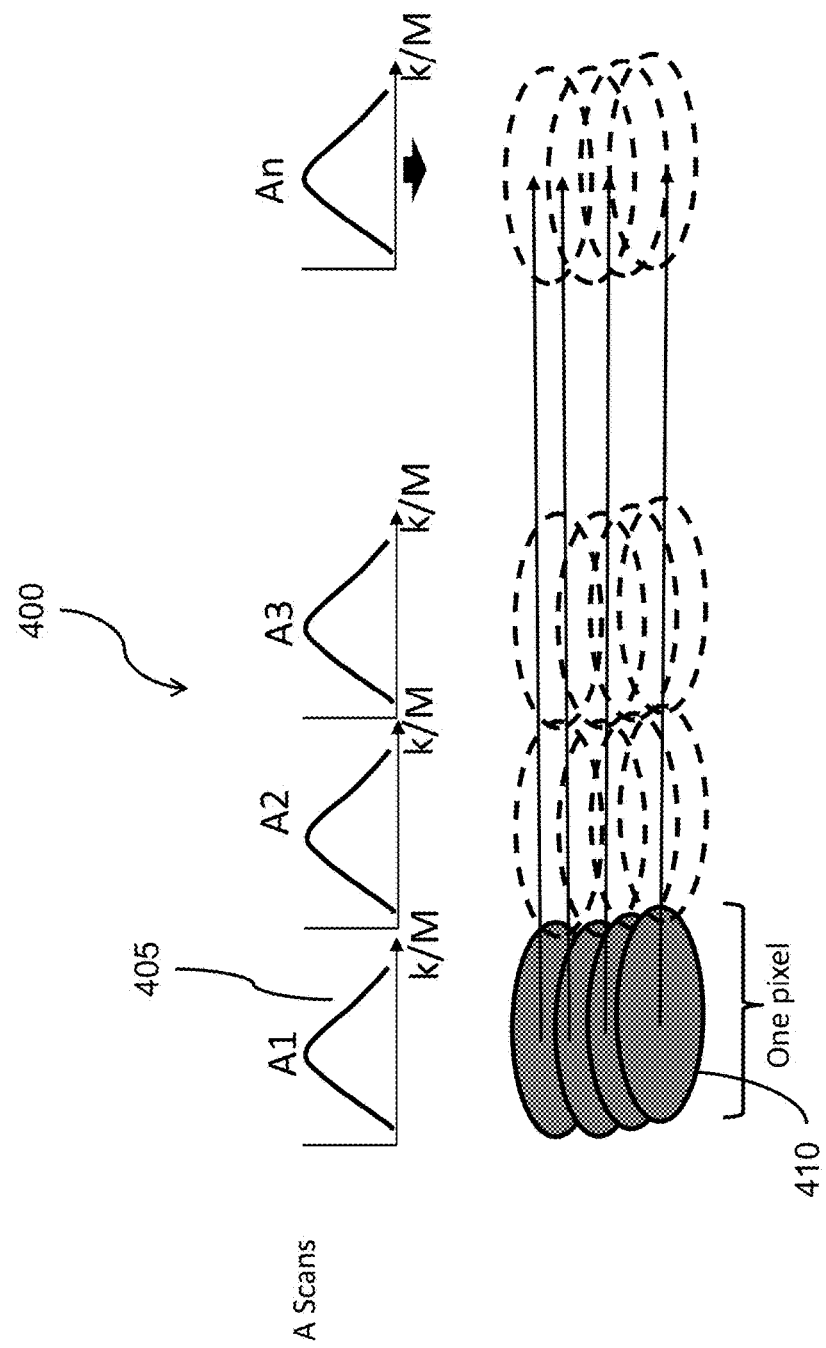
FIG. 4 depicts another graph that demonstrates flow imaging in accordance with an illustrative embodiment.

FIG. 4 depicts another graph 400 that demonstrates flow imaging in accordance with an illustrative embodiment. The graph 400 shows performing multiple B scans that have the same number of A scans per B scan (i.e., M=1). In this way, each of the N number of B scans have a single A scan at each pixel. However, different from FIG. 2, the A scans can be (like the method of FIG. 3) a partial spectrum segment with respect to a full spectrum of a swept source. Accordingly, the A scans of FIG. 4 can be performed faster than the A scans of FIG. 2. For example, if a 400 kHz frequency scan with a 25 nm wavelength is used in FIG. 4, then a scan that otherwise has the same parameters (8 B scans per slice, 200 A scans per B scan, etc.) of FIG. 2 may be completed in 25% of the time (e.g., 0.8 seconds instead of 3.2 seconds). While the resolution may be less, this may, in some circumstances or for certain applications be an acceptable or desirable trade off. In various embodiments, any subset of the full spectrum of the swept source may be utilized in this matter. Using the information reflected back from the sample, the system can determine a flow image in any of the ways disclosed herein. This mode could also be used to more quickly image structural aspects of a sample as well. This may be valuable for faster imaging, and may also be valuable for a preview so that a person can see a general location of where a flow image is going to be taken before a flow imaging mode is initiated. Accordingly, the OCT systems disclosed herein can be easily switched in and out of an efficient flow imaging mode.

FIG. 5 depicts a graph 500 that demonstrates amplitude-decorrelation and speckle variance methods for flow imaging in accordance with an illustrative embodiment. The corresponding A scans of different B scans (B1 and B2) are compared by the system to determine the flow image. The different B scans may be subsequent (same location but scanned at different times) or may be adjacent (B scans of slices of the sample next to or very near to each other). A represents the amplitude information, N is the number of B scans from the same slice position performed, and M is the number of A scans per pixel. An illustrative formula for amplitude-decorrelation determinations is shown below as Equation 1:

$$\overline{D}(x,z) = 1 - \frac{1}{N-1}\frac{1}{M}\sum_{n=1}^{N-1}\sum_{m=1}^{M}\frac{A_n(x,z)A_{n+1}(x,z)}{\left[\frac{1}{2}A_n(x,z)^2 + \frac{1}{2}A_{n+1}(x,z)^2\right]} \quad \text{Equation 1}$$

An illustrative formula for performing speckle variance is shown below as Equation 2:

$$\overline{D}(x,z) = \frac{1}{N-1}\frac{1}{M}\sum_{n=1}^{N-1}\sum_{m=1}^{M}(A_n(x,z) - A_{n+1}(x,z))^2 \quad \text{Equation 2}$$

Each of these formulas, as well as other methods, may be used to determine a flow image based on the OCT signals reflected back from a sample using the methods, systems, and computer readable medium disclosed herein.

Figure 6:
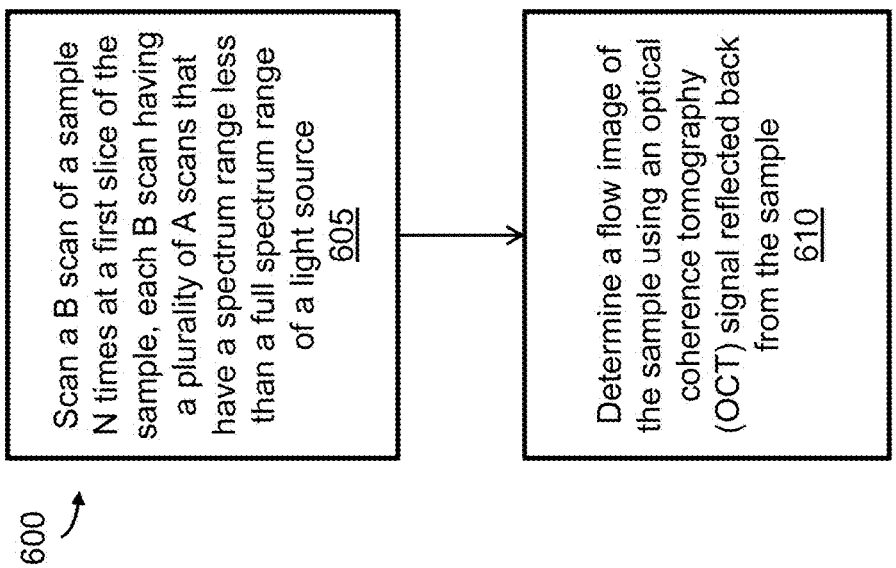
FIG. 6 depicts a flow diagram demonstrating a method for improved flow imaging in accordance with an illustrative embodiment.

FIG. 6 depicts a flow diagram demonstrating a method 600 for improved flow imaging in accordance with an illustrative embodiment. In an operation 605, the system scans a B scan of a sample N times at a first slice of the sample, each B scan having a plurality of A scans that have a spectrum range less than a full spectrum range of a light source. In an operation 610, the system determines a flow image of the sample using an optical coherence tomography (OCT) signal reflected back from the sample. The method 600 may be used for example, on either of the methods shown above with respect to FIGS. 3-5.

Figure 7:
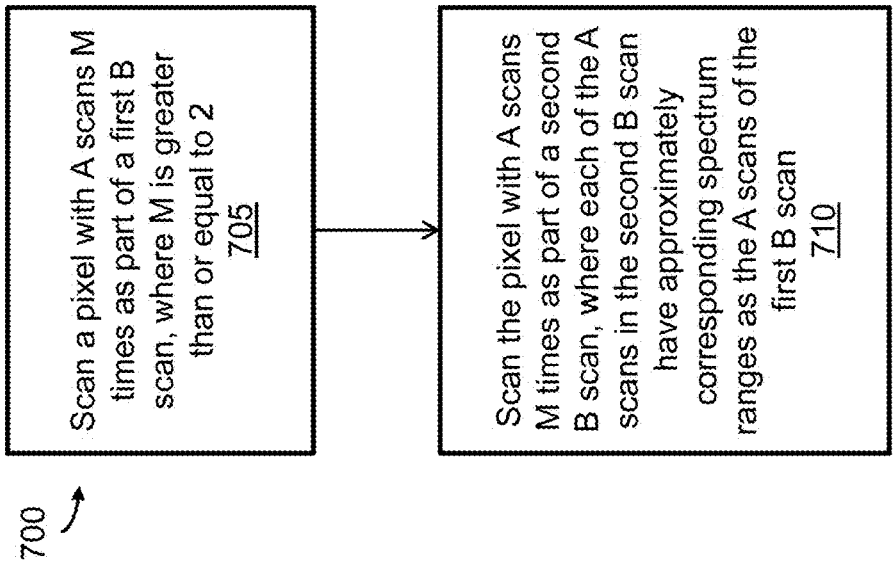
FIG. 7 depicts a flow diagram demonstrating a method for improved flow imaging in accordance with an illustrative embodiment.

FIG. 7 depicts a flow diagram demonstrating a method 700 for improved flow imaging in accordance with an illustrative embodiment. In an operation 705, the system scans a pixel with A scans M times as part of a first B scan, where M is greater than or equal to 2. In an operation 710, the system scans the pixel with A scans M times as part of a second B scan, where each of the A scans in the second B scan have approximately corresponding spectrum ranges as the A scans of the first B scan. This method corresponds to the graph shown and described above with respect to FIG. 3. Various methods may also be used to determine a flow diagram based on this info, such as those shown if FIG. 5 and discussed above.

Figure 8:
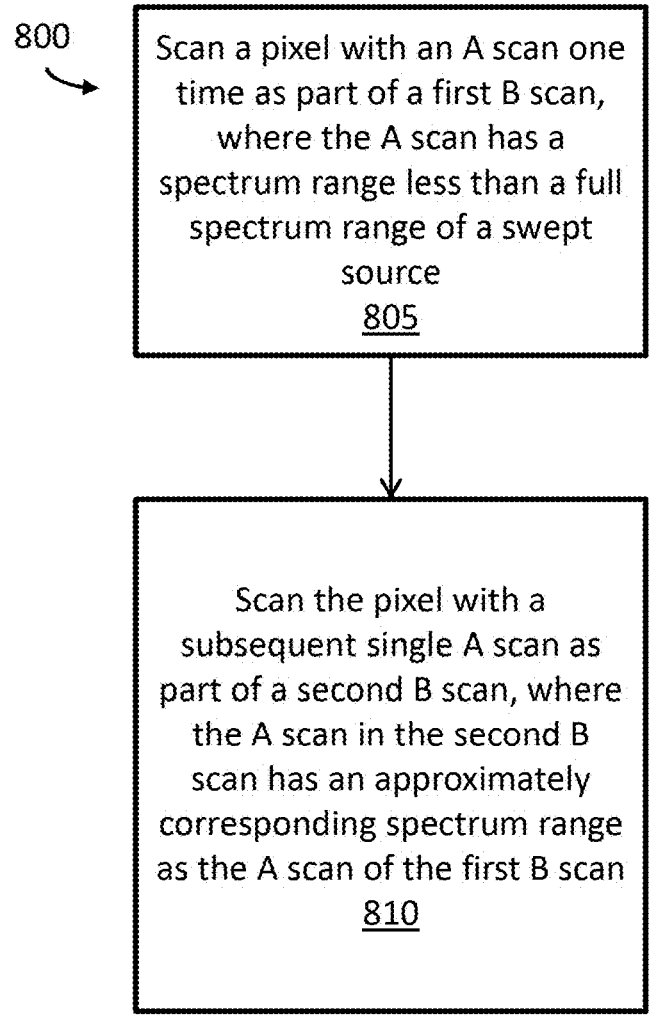
FIG. 8 depicts a flow diagram demonstrating a method for improved flow imaging in accordance with an illustrative embodiment.

FIG. 8 depicts a flow diagram demonstrating a method 800 for improved flow imaging in accordance with an illustrative embodiment. In an operation 805, the system scans a pixel with an A scan one time as part of a first B scan, where the A scan has a spectrum range less than a full spectrum range of a swept source. In an operation 810, the system scans the pixel with a subsequent single A scan as part of a second B scan, where the A scan in the second B scan has an approximately corresponding spectrum range as the A scan of the first B scan. This method corresponds to the graph shown and described above with respect to FIG. 4. Various methods may also be used to determine a flow diagram based on this info, such as those shown if FIG. 5 and discussed above.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in textincorporated by reference are excluded to the extent that they contradict definitions in this disclosure.

Other embodiments are set forth in the following claims.

What is claimed is:

1. An optical coherence tomography (OCT) system comprising:
    a light source configured to generate a probe beam having an adjustable swept rate and swept range;
    an interferometer and beam scanning optics configured to scan the probe beam onto a sample;
    a detector configured to measure an OCT interference signal returning from the sample;
    a processor configured to generate an OCT image of a flow of the sample, wherein the processor is configured to:
        scan a B scan of a sample N times at a first slice of the sample, wherein:
            N is greater than or equal to 2,
            the B scan comprises a plurality of A scans,
            a pixel of the first slice has an M number of A scans within the pixel,
            each of the A scans has a spectrum range less than a full spectrum range of the light source, and
            a number of pixels per B scan is an approximate B scan length divided by a lateral resolution size of the pixel; and
        determine a flow image of the sample using an optical coherence tomography (OCT) signal reflected back from the sample.

2. The OCT system of claim 1, wherein M is greater than 1.

3. The OCT system of claim 2, wherein the spectrum range of each of the A scans is approximately 1/M of the full spectrum of the light source.

4. The OCT system of claim 2, wherein each of the A scans within the pixel scans at a different spectrum range of the full spectrum.

5. The OCT system of claim 4, wherein determining the flow image further comprises performing speckle variance detection or amplitude-decorrelation of the OCT signal between corresponding A scans of the same spectrum range within the pixel.

6. The OCT system of claim 1, wherein the processor is configured to perform additional B scans of the sample at additional slices adjacent to the first slice.

7. The OCT system of claim 1, wherein determining the flow image further comprises detecting motion between consecutive B scans by comparing the N B scans to one another.

8. The OCT system of claim 1, wherein determining the flow image further comprises performing speckle variance detection or amplitude-decorrelation of the OCT signal of the M number of A scans.

9. The OCT system of claim 1, wherein determining the flow image further comprises performing speckle variance detection or amplitude-decorrelation of the OCT signal between the consecutive N B scans at the pixel.

10. The OCT system of claim 1, wherein determining the flow image further comprises averaging speckle variance detection or amplitude-decorrelation of the OCT signal over the M A scans of the pixel and/or over consecutive N B scans at the pixel.

11. The OCT system of claim 1, wherein M=1, wherein each of the N B scans at the pixel comprises a single A scan at the pixel.

12. The OCT system of claim 1, wherein each of the single A scans at the pixel performed N times have the same spectrum range of the light source.

13. A method for imaging comprising:
    scanning a B scan of a sample N times at a first slice of the sample, wherein:
        N is greater than or equal to 2,
        the B scan comprises a plurality of A scans,
        a pixel of the first slice has an M number of A scans within the pixel,
        each of the A scans has a spectrum range less than a full spectrum range of a light source, and
        a number of pixels per B scan is an approximate B scan length divided by a lateral resolution size of the pixel; and
    determining a flow image of the sample using M segments of an optical coherence tomography (OCT) signal reflected back from the sample.

14. The method of claim 13, wherein M is greater than 1, the spectrum range of each of the A scans is approximately 1/M of the full spectrum of the light source, and each of the A scans within the pixel scans at a different spectrum range of the full spectrum.

15. The method of claim 13, wherein determining the flow image further comprises performing speckle variance detection or amplitude-decorrelation of the OCT signal:
    between corresponding A scans of the same spectrum range within the pixel,
    of the M number of A scans, and/or
    between the consecutive N B scans at the pixel.

16. The method of claim 13, wherein determining the flow image further comprises averaging speckle variance detection or amplitude-decorrelation of the OCT signal over the M A scans of the pixel and/or over consecutive N B scans at the pixel.

17. A non-transitory computer readable medium having instructions thereon that, upon execution by a computing device, cause the computing device to perform operations comprising:
    scanning a B scan of a sample N times at a first slice of the sample, wherein:
        N is greater than or equal to 2,
        the B scan comprises a plurality of A scans,
        a pixel of the first slice has an M number of A scans within the pixel,
        each of the A scans has a spectrum range less than a full spectrum range of a light source, and
        a number of pixels per B scan is an approximate B scan length divided by a lateral resolution size of the pixel; and
    determining a flow image of the sample using M segments of an optical coherence tomography (OCT) signal reflected back from the sample.

18. The non-transitory computer readable medium of claim 17, wherein M is greater than 1, the spectrum range of each of the A scans is approximately 1/M of the full spectrum of the light source, and each of the A scans within the pixel scans at a different spectrum range of the full spectrum.

19. The non-transitory computer readable medium of claim 17, wherein determining the flow image further comprises performing speckle variance detection or amplitude-decorrelation of the OCT signal:
    between corresponding A scans of the same spectrum range within the pixel,
    of the M number of A scans, and/or
    between the consecutive N B scans at the pixel.

20. The non-transitory computer readable medium of claim 17, wherein determining the flow image further comprises averaging speckle variance detection or amplitude-decorrelation of the OCT signal over the M A scans of the pixel and/or over consecutive N B scans at the pixel.

* * * * *